United States Patent

Thoreau et al.

[11] Patent Number: 5,910,508
[45] Date of Patent: Jun. 8, 1999

[54] POLYCYCLIC POLYENIC COMPOUNDS AND PHARMACEUTICAL/COSMETIC COMPOSITIONS COMPRISED THEREOF

[75] Inventors: Etienne Thoreau, Saint Vallier De Thiey; Braham Shroot, Antibes, both of France

[73] Assignee: Centre International De Recherches Dermatologiques Galderma, Valbonne, France

[21] Appl. No.: 08/921,591

[22] Filed: Sep. 2, 1997

[30] Foreign Application Priority Data

Sep. 2, 1996 [FR] France .................. 96 10686

[51] Int. Cl.⁶ .............. A61K 31/38; A61K 31/19; C07D 335/04; C07C 62/06
[52] U.S. Cl. .............. 514/432; 514/456; 514/532; 514/569; 514/319; 514/428; 514/238.8; 514/297; 549/23; 549/407; 562/466; 560/61; 546/195; 544/177; 544/224
[58] Field of Search .................. 514/432, 456, 514/569, 532, 319, 428, 238.8, 297; 549/23, 407; 562/466; 560/61; 546/195; 544/177, 224; 548/570

[56] References Cited

U.S. PATENT DOCUMENTS 5,037,825  8/1991  Klaus et al. .................. 514/233.8
5,512,683  4/1996  Klaus et al. .................. 549/9

FOREIGN PATENT DOCUMENTS 0568898  11/1993  European Pat. Off. .
2390428  12/1978  France .
95/04036  2/1995  WIPO .

OTHER PUBLICATIONS

J. Med. Chem. (JMCMAR,00222623); 96; vol. 39, (17); pp. 3229–3234, Ligand Pharmaceuticals Inc.; Department of Retinoid Chemistry Research; San Diego, 92121 Calif.; XP002030143, 1996.

*Primary Examiner*—Deborah C. Lambkin
*Attorney, Agent, or Firm*—Burns, Doane, Swecker & Mathis, L.L.P.

[57] ABSTRACT

Novel pharmaceutically/cosmetically-active polycyclic polyenic compounds have the structural formula (I):

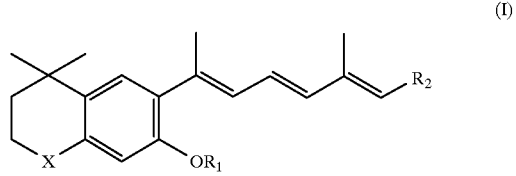

and are useful for modulating cellular hormone receptors.

18 Claims, 1 Drawing Sheet

POLYCYCLIC POLYENIC COMPOUNDS AND PHARMACEUTICAL/COSMETIC COMPOSITIONS COMPRISED THEREOF

BACKGROUND OF THE INVENTION

1. Technical Field of the Invention

The present invention relates to novel polycyclic polyenic compounds that modulate families of cellular hormone receptors such as those described by Guiguère or Evans (Guiguère V., *Endocrine Reviews*, 15,1, 61 (1994); Mangelsdorf D. & Evans R., *Cell*, 83, 841 (1995)) and to pharmaceutical/cosmetic compositions comprised thereof.

SUMMARY OF THE INVENTION

On the basis of the above indicated interaction, the subject novel compounds exert biological activity with respect to animal cells and tissues relative to their differentiation, their proliferation or their involvement in cell death (apoptosis). These species act in combination with known ligands of the superfamily, for example retinoic acid and retinoids, vitamin $D_3$, thyroid hormone, estrogens and the like, to enhance their risk/benefit ratio, both by reducing their toxicity and by improving their pharmacological efficacy.

The compounds according to the invention are useful for the prevention and/or treatment of disorders and/or afflictions associated with an overregulation of the receptors linked to these hormones or vitamins. They may also be involved in the control of the different steps of the metabolism or catabolism of these hormones or vitamins.

Briefly, the polycyclic polyenic compounds according to the present invention have the following structural formula (I):

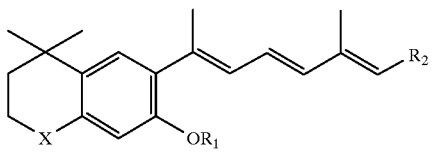

in which X is a bivalent radical $>C(CH_3)_2$, an oxygen atom (—O—) or a sulfur atom (—S—); $R_1$ is a radical of formula —$(CH_2)_n$—Z—$(CH_2)_o$—Y, wherein Z, Y, n and o are as defined below; Y is —OH, a thiol radical (—SH), a trimethylammonium radical (—$N^+(CH_3)_3$), a cyano radical (—CN), a radical —$COR_3$, or an —$NH_2$ radical, wherein $R_3$ is as defined below; Z is a methylene radical (—$CH_2$—) or an oxygen atom (—O—); $R_2$ is a radical —$COR_3$ or —$CH_2$—OH; $R_3$ is a hydrogen atom, a hydroxyl radical, a lower alkoxy or cycloalkoxy radical, or a radical of formula —$NR_4R_5$; $R_4$ and $R_5$, which may be identical or different, are each a hydrogen atom or a lower alkyl radical, or $R_4$ and $R_5$ together form a heterocycle with the nitrogen atom from which they depend; and n and o, which may be identical or different, are each an integer ranging from 1 to 5.

This invention also features the pharmaceutically acceptable salts of the compounds of formula (I), as well as the racemates and optical and geometric isomers or mixtures thereof, in all proportions.

BRIEF DESCRIPTION OF THE DRAWING

The FIGURE of Drawing sets forth reaction schemes/mechanisms illustrating representative syntheses for the preparation of the polycyclic polyenic compounds according to the present invention.

DETAILED DESCRIPTION OF BEST MODE AND SPECIFIC/PREFERRED EMBODIMENTS OF THE INVENTION

Figure 1:
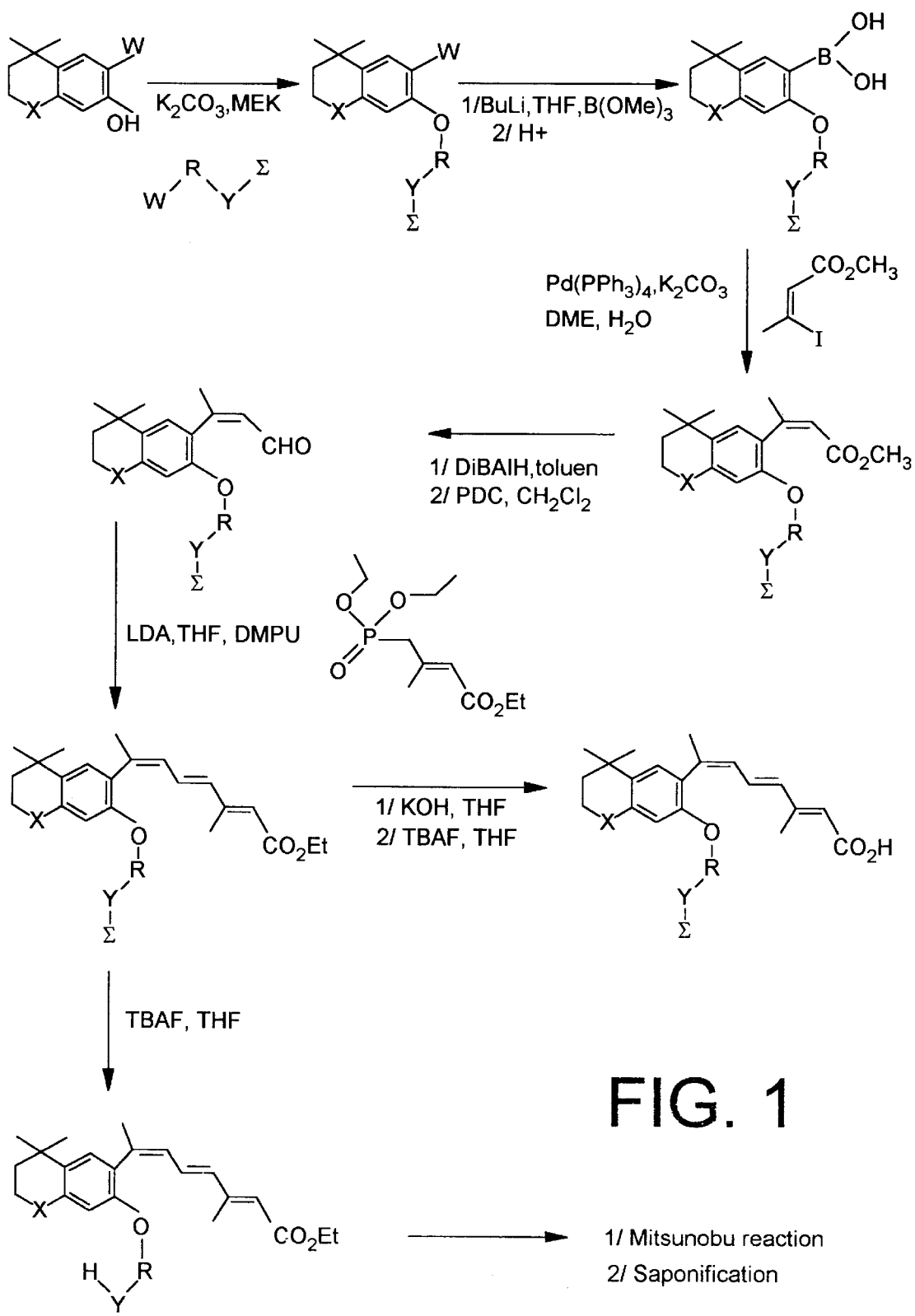

More particularly according to the present invention, when the subject compounds exist in the form of salts, they are preferably salts of an alkali metal or alkaline earth metal, or, alternatively, of zinc or of an organic amine.

By the term "lower alkyl radical" is intended a linear or branched alkyl radical having from 1 to 6 carbon atoms, preferably methyl, ethyl, isopropyl, butyl, tert-butyl and hexyl radicals. This definition is also applicable to the alkyl moieties of the alkoxy radicals.

By "cycloalkoxy" is preferably intended a radical in which the cycloalkyl moiety is a mono- or polycyclic group having from 3 to 12 carbon atoms, optionally substituted with one or more lower alkyl radicals.

By "heterocycle" is preferably intended a piperidino, morpholino, pyrrolidino or piperazino radical, optionally substituted in the 4-position by a lower alkyl radical.

Preferably, when Z is an oxygen atom (—O—), then Y is a cyano radical (—CN) or a radical —$COR_3$, wherein $R_3$ is as defined above, n is 2, 3 or 4 and o is 1, 2 or 3.

In another preferred embodiment of the invention, when Z is a methylene radical (—$CH_2$—), then Y is a thiol (—SH), trimethylammonium (—$N^+(CH_3)_3$) or cyano (—CN) radical.

The compounds of formula (I) are readily prepared, in particular, by reacting a hydroxyl compound of formula (II)

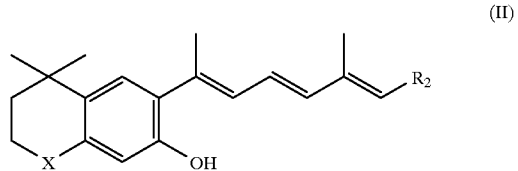

in which X and $R_2$ are as defined above, with a compound of formula (III)

$$X—(CH_2)_n—Z—(CH_2)_o—Y \quad (III)$$

in which Z, Y, n and o are as defined above, and X is a leaving group such as a halogen, especially bromine or iodine.

The hydroxyl compound of formula (II) is itself prepared from the corresponding alkoxy derivative described in DE-2,819,213, in particular the methoxy derivative described in Example 9. Hydrolysis of the ether function is carried out according to standard techniques in the art, with protection and suitable deprotection of the functions which are sensitive to the hydrolysis conditions.

In particular, when $R_2$ is a —COOH radical, the compounds are prepared by protecting $R_2$ with a protective group of the alkyl, allyl, benzyl or tertbutyl type.

Conversion to the free form may be carried out:

(i) in the case of an alkyl protective group, by means of sodium hydroxide or lithium hydroxide in an alcoholic solvent such as methanol or in THF;

(ii) in the case of an allyl protective group, by means of a catalyst such as certain transition metal complexes in the presence of a secondary amine such as morpholine;

(iii) in the case of a benzyl protective group, by debenzylation in the presence of hydrogen by means of a catalyst such as palladium on charcoal;

(iv) in the case of a tert-butyl type protective group, by means of trimethylsilane iodide.

Advantageously, the phenol of general formula (II) is converted into the compound of formula (I) via reaction with the compound of formula (III) in the presence of potassium carbonate in methyl ethyl kektone, or in the presence of sodium hydride in a solvent, such as dimethyl formamide.

The compounds of formula (I) may also be prepared according to the reaction scheme shown in the Figure of Drawing. In this Figure: W is a halogen atom, such as bromine or iodine, E is a protecting group, such as tertbutyl dimethyl silane (TBDMSi), R is the radical —$(CH_2)_n$—Z—$(CH_2)_o$ and Y is as described above. The Mitsunobu and saponification reactions are eventually performed if Y is the oxygen atom and substitution thereof into a sulfur or nitrogen atom is desired.

The present invention also features cosmetic or pharmaceutical compositions comprising at least one compound of general formula (I), and at least one cosmetically or pharmaceutically acceptable vehicle, diluent or carrier therefor.

The cosmetic or pharmaceutical compositions containing at least one compound of formula (I) are especially well suited for the treatment of disorders or afflictions/conditions associated with an overregulation of the transcription factors designated retinoid receptors which comprise the RARs (retinoic acid receptors), including the subtypes α, β and γ, the retinoic X receptors (RXRs), including the subtypes α, β and γ or the genes comprising the RAR and RXR response elements.

By "overregulation of the RAR and/or RXR receptors" is intended an overexpression of the RAR and/or RXR receptors, and/or a biological overactivity of the RAR and/or RXR receptors.

Biological overactivity of the RAR and/or RXR receptors may be due to a chemical modification of the RAR and/or RXR receptors, but it may also be due to a factor other than the receptor itself. Thus, the biological overactivity may be due to the overexpression of an endogenous gene, or to the expression of an exogenous gene comprising the response element RARE (retinoic acid response element) to which a heterodimer comprising the RAR receptor has become bound, the latter having an agonist ligand. One example of overexpression of an endogenous gene comprising the response element RARE is the CRABP II (cellular retinoic acid binding protein II) gene whose overexpression has been demonstrated in psoriasis ("Overexpression of CRABP II and down-regulation of CRABP I in psoriatic skin", G. Siegenthaler et al., *Dermatology*, 185, 251–256 (1992)). And one example of expression of an exogenous gene comprising the response element RARE is the HIV-1 (human immunodeficiency virus) genome (Lee et al., *Proc. Natl. Acad. Sci. USA*, Vol. 91, pp. 2632–5636 (June 1994)) or the hepatitis B virus genome ("Retinoid X receptor RXR alpha binds to and transactivates the hepatitis B virus enhancer", B. Huan et al., *Proc. Natl. Acad. Sci. USA*, 89 (19), pp. 9059–63 (1992)).

These disorders and/or afflictions associated with an overregulation of the RAR and/or RXR receptors manifest themselves more often than not in an inflammatory, allergic and/or immunological component. They exist, more especially, in the following pathologies or disorders:

(1) Acne vulgaris, comedonic or polymorphic acne, rosacea, nodulocystic acne, acne conglobata, senile acne and secondary acnes such as solar, drug-induced or occupational acne, (2) Other types of keratinization disorders, in particular ichthyoses, ichthyosiform conditions, Darier's disease, palmoplantar keratoderma, leucoplakia and leucoplakiform conditions and cutaneous or mucosal (buccal) lichen, (3) Other dermatological conditions associated with a keratinization disorder manifesting an inflammatory and/or immunoallergic component, and in particular all forms of psoriasis, whether cutaneous, mucosal or ungual, and even arthropathia psoriatica, or alternatively cutaneous atopy such as eczema, or respiratory atopy or gingival hypertrophy, (4) Certain inflammatory conditions not entailing a keratinization disorder, such as arthritis, (5) Dermal or epidermal proliferations, whether benign or malignant, whether or not of viral origin, such as common warts, flat warts and epidermodysplasia verruciformis, oral or florid papillomatoses and proliferations which may be induced by ultraviolet light, in particular in the case of basal cell and prickle cell epithelioma, (6) Other dermatological disorders such as vesicular dermatoses and collagen diseases, (7) Certain ophthalmological disorders, in particular corneopathies, (8) Skin aging, whether photoinduced or natural, or actinic keratosis and pigmentations, or all pathologies associated with natural or actinic aging, (9) The stigmata of epidermal and/or dermal atrophy induced by local or systemic corticosteroids, or any other form of cutaneous atrophy,

(10) Disorders of cicatrization, or stretch marks,

(11) Disorders of sebaceous function, such as hyperseborrhoea associated with acne or simple seborrhoea,

(12) Cancerous or precancerous conditions,

(13) Disease states of viral origin, affecting the skin or generally (human immunodeficiency virus, HIV-1, or hepatitis B virus),

(14) Alopecia,

(15) Afflictions of the cardiovascular system such as arteriosclerosis,

(16) Skin conditions caused by irradiation, more especially solar irradiation, such as benign summer leucitis, light-induced herpes labialis, solar erythema or photoinduced immunosuppressant effects.

According to the present invention, the compounds of formula (I) may advantageously be employed in combination with other compounds exhibiting retinoid type activity, with D vitamins or derivatives thereof, with corticosteroids, with free-radical scavengers, with α-hydroxy or α-keto acids or derivatives thereof, or with ion-channel blockers. By "D vitamins or derivatives thereof" are intended, for example, vitamin $D_2$ or $D_3$ derivatives, and especially 1,25-dihydroxyvitamin $D_3$. By "free-radical scavengers" are intended, for example, α-tocopherol, superoxide dismutase, ubiquinol or certain metal chelators. By "α-hydroxy or α-keto acids or derivatives thereof" are intended, for example, lactic, malic, citric, glycolic, mandelic, tartaric, glyceric or ascorbic acids or their salts, amides or esters. Lastly by "ion-channel blockers" are intended, for example, minoxidil (2,4-diamino-6-piperidino-pyrimidine 3-oxide) and derivatives thereof.

The cosmetic or pharmaceutical compositions comprising an effective amount of at least one compound of formula (I), or at least one of the isomers (optical or geometric) or salts thereof also comprise a cosmetically or pharmaceutically acceptable vehicle, diluent or carrier therefor which is compatible with the mode of administration desired.

Since the effective amount naturally depends on the desired treatment and the nature of the compound selected, it is readily determined by one skilled in this art.

The administration of the compounds according to the invention may be performed via the enteral, parenteral, systemic, topical or ocular route.

For enteral administraton, the pharmaceutical compositions, are advantageously formulated as tablets, hard gelatin capsules, dragées, syrups or suspensions, elixers, solutions, powders, granules, emulsions, microspheres or nanospheres or lipid or polymer vesicles, permitting controlled release. For parenteral administration, the subject compositions, more especially the pharmaceutical compositions, are advantageously formulated as solutions or suspensions for perfusion or for injection.

The compounds according to the invention are generally administered to mammalian subjects at a daily dosage of approximately 0.01 mg/kg to 100 mg/kg body weight, and this at the rate or regimen of 1 to 3 doses per diem.

For topical administration, the subject compositions are more especially intended for the treatment of the skin and the mucosae, and are advantageously formulated as ointments, creams, milks, salves, powders, impregnated pads, solutions, gels, sprays, lotions, suspensions or shampoos. They may also be formulated as microspheres or nanospheres or lipid or polymer vesicles, or as polymer patches and hydrogels permitting controlled release. The compositions for topical application can, moreover, be either in anhydrous form or in an aqueous form.

For ocular administration, the subject compositions are advantageously eyewashes.

The compositions for topical or ocular application contain at least one compound of formula (I), or one of its chiral or geometric analogs or one of its salts, at a concentration preferably ranging from 0.001% to 5% by weight relative to the total weight of the composition.

The compositions according to the invention can, in addition, contain inert or even pharmacodynamically or cosmetically active additives and adjuvants, or combinations of these additives and adjuvants, and in particular: wetting agents; depigmenting agents such as hydroquinone, azelaic acid, caffeic acid or kojic acid; emollients; hydrating agents such as glycerol, PEG 400, thiamorpholinone and derivatives thereof or, alternatively, urea; antiseborrhoeic or anti-acne agents such as S-carboxymethylcysteine, S-benzylcysteamine, or salts or derivatives thereof, or benzoyl peroxide; antibiotics such as erythromycin and its esters, neomycin, clindamycin and its esters, tetracyclines; antifungal agents such as ketoconazole and 4,5-polymethylene-3-isothiazolidones; hair restorers such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids, and β-carotene in particular; antipsoriatic agents such as anthralin and derivatives thereof; and, lastly, 5,8,11,14-eicosatetraynoic and 5,8,11-eicosatriynoic acids, and esters and amides thereof.

The subject compositions can also contain flavor enhancers, preservatives such as parahydroxybenzoic acid esters, stabilizing agents, moisture-regulating agents, pH-regulating agents, osmotic pressure-modifying agents, emulsifying agents, UV-A and UV-B screening agents and antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLE 1

Synthesis of (E,E,Z)-7-[3-(5-hydroxpentyloxy)-5,5,8,8-tetramethyl-5,6,7,8-tetrahydro-2-naphthyl]-3-methyl-2,4,6,-octatrienoic acid

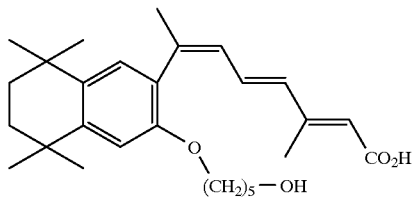

(a) Preparation of 5-(3-bromo-5,5,8,8-tetramethyl-5,6,7,8-tetrahydro-2-napthyloxy)pentyl acetate A solution of 3-bromo-5,5,8,8-tetramethyl-5,6,7,8-tetrahydro-2-naphthol (10 g, 0.35 mol), 5-bromopentyl acetate (8.15 g) and potassium carbonate (33.6 g) in methyl ethyl ketone (MEK) (200 ml) was heated to reflux for 2 hours. The reaction medium was treated with water and ethyl acetate. After settling, the organic phase was separated and washed twice with water, dried over magnesium sulfate and concentrated in a rotary evaporator under vacuum at 40° C. The desired compound was purified by flash chromatography on a silica column.

Yellow oil. Yield: 93%.

(b) Preparation of [5-(3-bromo-5,5,8,8-tetramethyl-5,6,7,8-tetrahydro-2-naphythyloxy)pentyloxy]-tert-butyldimethylsilane The acetate obtained in (a) above was saponified, and the resulting hydroxyl group was then protected according to the following procedure: tert-butyldimethylsilyl chloride (2.64 g) was added to a mixture of 5-(3-bromo-5,5,8,8-tetramethyl-5,6,7,8-tetrahydro-2-naphthyloxy)-1-pentanol (4.3 g, 11.7 mmol) and 80% sodium hydride (422 mg) in THF (20 ml). The mixture was stirred at room temperature for 2 h. The solution was poured into a mixture of water and ethyl acetate. The organic phase was washed twice with water, dried over magnesium sulfate and concentrated in a rotary evaporator under vacuum at 40° C. The desired compound was purified by flash chromatography on a silica column.

Yellow oil. Yield: 64%.

(c) Preparation of 3-[5-(tert-butyldimethylsilyloxy)pentyloxy]-5,5,8,8-tetramethyl-5,6,7,8-tetrahydro-2-naphtaleneboronic acid A 2.5M solution of butyllithium (BuLi) in hexane (0.45 ml, 1.12 mmol) was added dropwise to a solution of the compound obtained in (b) above (500 mg, 1.03 mmol) in THF (2 ml) at −78° C. Stirring was continued for 0.5 h at the same temperature, and trimethoxyl borate (0.35 ml) was then added dropwise at −78° C. Stirring was continued for 3 h at −78° C., and the reaction medium was then hydrolyzed at −40° C. with saturated NH$_4$Cl solution. The mixture was extracted with ethyl ether, washed twice with water, dried and concentrated in a rotary evaporator under vacuum.

Colorless oil. Yield: 75%.

(d) Preparation of methyl (Z)-3-{3-[5-(tert-butyldimethylsilyloxy)-pentyloxy]-5,5,8,8-tetramethyl-5,6,7,8-tetrahydro-2-naphthyl}-2-butenoate A mixture of tetrakis(triphenyl-phosphine)palladium (155 mg), 3-[5-(tert-butyldimethylsilyloxy)pentyloxy]-5,5,8,8-tetramethyl-5,6,7,8-tetrahydro-2-naphthaleneboronic acid (300 mg, 0.67 mmol), a 2M solution of potassium carbonate in water (0.67 ml) and methyl (Z)-3-iodo-2-butenoate (Ma, S. & Lu, X.; *J. Chem. Soc. Chem. Com.*, pp. 1643–1644 (1990)) (182 mg) in dimethoxyethane (DME) (10 ml) was heated to reflux for 24 h. The solution was poured into a mixture of water and ethyl acetate. The organic phase was washed twice with water, dried over magnesium sulfate and concentrated in a rotary evaporator under vacuum at 40° C. The desired compound was purified by flash chromatography on a silica column.

Colorless oil. Yield: 80%.

NMR δ ppm: $^1$H/CDCl$_3$: –0.012 (s, 6H); 0.92 (s, 9H); 1.18 to 1.25 (m, 12H); 1.36 to 1.57 (m, 4H); 1.60 (s, 3H); 1.65 to 1.74 (m, 2H); 2.12 (d, 3H); 3.45 (s, 3H); 3.57 (t, 2H); 3.87 (t, 3H); 5.85 (d, 1H); 6.69 (s, 1H); 6.88 (s, 1H).

(e) Preparation of (Z)-3-{3-[5-(tert-butyldimethylsilyloxy)pentyloxy]-5,5,8,8-tertramethyl-5,6,7,8,-tetrahydro-2-naphthyl}-2-butenal A 1M solution of diisobutylaluminum hydride (DiBAlH) in toluene (3.8 ml) was added dropwise at 0° C. to a solution of methyl (Z)-3-{3-[5-(tert-butyldimethylsilyloxy)pentyloxy]-5,5,8,8-tetramethyl-5,6,7,8-tetrahydro-2-naphthyl}-2-butenoate (1.9 g, 37.8 mmol) in toluene (40 ml). The mixture was stirred for 1 h at room temperature, then treated with sodium potassium double tartrate solution and filtered. The filtrate was poured into an ethyl ether/water mixture. The organic phase was washed with water, dried over anhydrous magnesium sulfate and concentrated in a rotary evaporator under vacuum at 40° C. The resulting oil was solubilized in 30 ml of dichloromethane, and 2 g of pyridinium dichromate (PDC) were added. The mixture was stirred for 4 h at room temperature and filtered through silica. The filtrate was concentrated in a rotary evaporator under vacuum at 40° C. and purified by flash chromatography on a silica column.

Colorless oil. Yield: 61%.

NMR δ ppm: $^1$H/CDCl$_3$: 0.00 (s, 6H); 0.84 (s, 9H); 1.18 to 1.25 (m, 12H); 1.44 to 1.50 (m, 4H); 1.63 (s, 3H); 1.66 to 1.74 (m, 2H); 2.23 (d, 3H); 3.57 (t, 2H); 3.89 (t, 3H); 6.04 (d, 2H/J=6.96); 6.74 (s, 1H); 6.94 (s, 1H); 9.31 (d, 1H).

(f) Preparation of ethyl (E,E,Z)-7-{3-[5-(tert-butyldimethylsilyloxy)-pentyloxy]-5,5,8,8-tetramethyl-5,6,7,8-tetrahydro-2-naphthyl}-3-methyl-2,4,6,-octatrienoate A 2.5M solution of BuLi in hexane (1.12 mmol) was added dropwise to a solution of diisopropylamine (387 μl) in a 1,3-dimethyl-3,4,5,6-tetrahydro-2(1H)-pyrimidinone (DMPU)/THF (10 ml/10 ml) mixture at –20° C. The mixture was stirred for 30 min at –20° C., and triethyl 3-methyl-4-phosphonocrotonate (0.68 ml) was then added. The mixture was stirred for 1 h at –20° C. and was added to a solution of (Z)-3-{3-[5-(tert-butyldimethylsilyloxy)pentyloxy]-5,5,8,8-tetramethyl-5,6,7,8-tetrahydro-2-naphthyl}-2-butenal (1.1 g, 2.3 mmol) in THF (5 ml). The reaction medium was permitted to warm to room temperature and was then treated with ethyl acetate/water. After settling, the organic phase was separated and washed twice with water, dried over anhydrous magnesium sulfate and concentrated in a rotary evaporator under vacuum at 40° C. The desired compound was purified by flash chromatography on a silica column.

Colorless oil. Yield: 84%.

NMR δ ppm: $^1$H/CDCl$_3$: 0.00 (s, 6H); 0.85 (s, 9H); 1.19 to 1.25 (m, 15H); 1.39 to 1.49 (m, 4H); 1.64 (s, 4H); 1.69 to 1.82 (m, 2H); 2.09 (s, 3H); 2.14 (s, 3H); 3.57 (t, 2H); 3.90 (t, 2H); 4.12 (q, 2H); 5.68 (s, 1H); 6.13 to 6.19 (m, 2H); 6.51 to 6.62 (m, 1H); 6.75 (s, 1H); 6.92 (s, 1H)

(g) Preparation of (E,E,Z)-7-{3-[5-(tert-butyldimethylsilyloxy)pentyloxy]-5,5,8,8-tetramethyl-5,6,7,8-tetrahydro-2-naphythyl}-3-methyl-2,4,6-octatrienoic acid A solution of ethyl (E,E,Z)-7-{3-[5-(tert-butyldimethylsilyloxy)pentyloxy]-5,5,8,8-tetramethyl-5,6,7,8-tetrahydro-2-naphthyl}-3-methyl-2,4,6-octatrienoate (880 mg) and potassium hydroxide (880 mg) in 22 ml of a THF/methanol/water (20/1/1) mixture was heated to reflux for 4 h. After concentration in a rotary evaporator under vacuum at 40° C., ethyl acetate and water were added. The mixture was acidified to pH 1 with concentrated hydrochloric acid solution. After settling, the organic phase was separated and washed twice with water, dried over anhydrous magnesium sulfate and concentrated in a rotary evaporator under vacuum at 40° C.

Colorless oil. Yield: 100%.

NMR δ ppm: $^1$H/CDCl$_3$: 0.00 (s, 6H); 0.85 (s, 9H); 1.22 to 1.26 (m, 15H); 1.38 to 1.51 (m, 4H); 1.55 (s, 4H); 1.63 to 1.79 (m, 2H); 2.05 (s, 3H); 2.15 (s, 3H); 3.57 (t, 2H); 3.89 (t, 2H); 5.70 ( , 1H); 6.16 to 6.22 (m, 2H); 6.56 to 6.66 (q, 1H); 6.74 (s, 1H); 6.91 (s, 1H).

(h) Synthesis of (E,E,Z)-7-[3-(5-hydroxypentyloxy)-5,5,8,8-tetramethyl-5,6,7,8-tetrahydro-2-naphthyl]-3-methyl-2,4,6-octatrienoic acid A mixture of (E,E,Z)-7-{3-[5-(tert-butyldimethylsilyloxy)pentyloxy]-5,5,8,8-tetramethyl-5,6,7,8-tetrahydro-2-naphthyl}-3-methyl-2,4,6-octatrienoic acid (850 mg, 1.5 mmol) and a 1M solution in THF of tetrabutylammonium fluoride (TBAF) (3.1 ml) in THF (10 ml) was stirred at room temperature for 1 h and then treated with ethyl acetate and with water. After settling, the organic phase was separated and washed twice with water, dried over anhydrous magnesium sulfate and concentrated in a rotary evaporator under vacuum at 40° C.

NMR δ ppm: $^1$H/CDCl$_3$: 1.23 to 1.30 (m, 12H); 1.48 to 1.65 (m, 4H); 1.68 (s, 4H); 1.73 to 1.86 (m, 2H); 2.14 (s, 3H); 2.18 (s, 3H); 3.65 (t, 2H); 3.94 (t, 2H); 5.74 (s, 1H); 6.20 to 6.26 (m, 2H); 6.56 to 6.69 (m, 1H); 6.96 (s, 1H); 7.26 (s, 1H).

EXAMPLE 2

Synthesis of ethyl (E,E,Z)-7-[3-(5-hydroxpentyloxy)-5,5,8,8-tetramethyl-5,6,7,8-tetrahydro-2-naphthyl]-3-methyl-2,4,6-octatrienoate

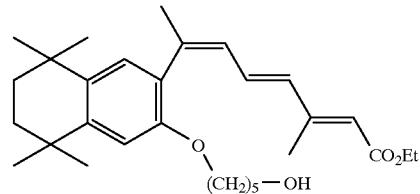

A mixture of ethyl (E,E,Z)-7-{3-[5-(tert-butyldimethylsilyloxy)pentyloxy]-5,5,8,8-tetramethyl-5,6,7,8-tetrahydro-2-naphthyl}-3-methyl-2,4,6-octatrienoate (250 mg) and a 1M solution in THF of tetrabutylammonium fluoride (0.85 ml) in THF (5 ml) was stirred at room temperature for 1 h and then treated with ethyl acetate and with water. After settling, the organic phase was separated and washed twice with water, dried over anhydrous magnesium sulfate and concentrated in a rotary evaporator under vacuum at 40° C.

Colorless oil. Yield: 35%.

NMR δ ppm: $^1$H/CDCl$_3$: 1.17 to 1.26 (m, 15H); 1.39 to 1.46 (m, 4H); 1.58 (s, 4H); 1.63 to 1.74 (m, 2H); 2.04 (s, 3H); 2.08 (s, 3H); 3.55 (t, 2H); 3.85 (t, 2H); 4.04 (q, 2H);

5.63 (s, 1H); 6.08 to 6.14 (m, 2H); 6.44 to 6.55 (m, 1H); 6.69 (s, 1H); 6.87 (s, 1H).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polycyclic polyenic compound having the structural formula (I):

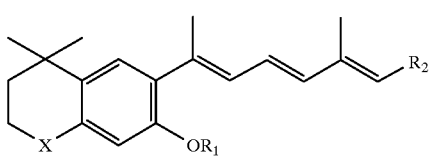

(I)

in which X is a bivalent radical >C(CH$_3$)$_2$, an oxygen atom (—O—) or a sulfur atom (—S—); R$_1$ is a radical of formula —(CH$_2$)$_n$—Z—(CH$_2$)$_o$—Y, wherein Z, Y, n and o are as defined below; Y is —OH, a thiol radical (—SH), a trimethylammonium radical (—N$^+$(CH$_3$)$_3$), a cyano radical (—CN), a radical —COR$_3$, or an —NH$_2$ radical, wherein R$_3$ is as defined below; Z is a methylene radical (—CH$_2$—) or an oxygen atom (—O—); R$_2$ is a radical —COR$_3$ or —CH$_2$—OH; R$_3$ is a hydrogen atom, a hydroxyl radical, a lower alkoxy or cycloalkoxy radical, or a radical of formula —NR$_4$R$_5$; R$_4$ and R$_5$, which may be identical or different, are each a hydrogen atom or a lower alkyl radical, or R$_4$ and R$_5$ together form a heterocycle with the nitrogen atom from which they depend; and n and o, which may be identical or different, are each an integer ranging from 1 to 5; or a pharmaceutically/cosmetically acceptable salt or optical or geometric isomer thereof.

2. The polycyclic polyenic compound as defined by claim 1, wherein formula (I), X is the bivalent radical >C(CH$_3$)$_2$.

3. The polycyclic polyenic compound as defined by claim 1, wherein formula (I), X is an oxygen atom.

4. The polycyclic polyenic compound as defined by claim 1, wherein formula (I), X is a sulfur atom.

5. The polycyclic polyenic compound as defined by claim 1, wherein formula (I), Z is an oxygen atom, Y is a cyano radical or a radical —COR$_3$, n is 2, 3 or 4, and o is 1, 2 or 3.

6. The polycyclic polyenic compound as defined by claim 1, wherein formula (I), Z is a methylene radical and Y is a thiol, trimethylammonium or cyano radical.

7. A pharmaceutical/cosmetic composition of matter, comprising an effective cellular hormone receptor-modulating amount of the polycyclic polyenic compound as defined by claim 1, or pharmaceutically/cosmetically acceptable salt or isomer thereof, formulated into a pharmaceutically/cosmetically acceptable vehicle, carrier or diluent therefor.

8. The pharmaceutical/cosmetic composition as defined by claim 7, comprising from 0.001% to 5% by weight of said polycyclic polyenic compound, or salt or isomer thereof.

9. The pharmaceutical/cosmetic composition as defined by claim 7, further comprising a retinoid compound, a D vitamin or derivative thereof, a corticosteroid, an anti-free radical agent, an α-hydroxy or α-keto acid or derivative thereof, an ion channel blocker, or combination thereof.

10. The pharmaceutical/cosmetic composition as defined by claim 7, comprising a tablet, a capsule, a syrup, a dragée, a suspension, an elixir, a solution, a powder, granules, an emulsion, microspheres, nanospheres, lipid vesicles, polymeric vesicles, or an injectable.

11. The pharmaceutical/cosmetic composition as defined by claim 7, comprising an ointment, a cream, a milk, a salve, an impregnated pad, a gel, a spray, or a lotion.

12. The pharmaceutical/cosmetic composition as defined by claim 4, adopted for topical application.

13. The pharmaceutical/cosmetic composition as defined by claim 7, adopted for systemic administration.

14. The pharmaceutical/cosmetic composition as defined by claim 7, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

15. The pharmaceutical/cosmetic composition as defined by claim 7, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

16. A regimen for modulating cellular hormone receptors in a mammalian organism in need of such treatment, comprising administering thereto an effective amount of the pharmaceutical/cosmetic composition as defined by claim 7.

17. The regimen as defined by claim 16, for treating a disorder/affliction manifesting an overregulation of the transcription factors designated retinoid receptors which comprise the RARs (retinoic acid receptors), including the subtypes α, β and γ, the retinoic X receptors (RXRs), including the subtypes α, β and γ, or the genes comprising the RAR and RXR response elements.

18. The regimen as defined by claim 16, for treating acne vulgaris, comedonic or polymorphic acne, rosacea, nodulocystic acne, acne conglobata, senile acne, secondary acne, a keratinization disorder, ichthyoses, an ichthyosiform condition, Darier's disease, palmoplantar keratoderma, leucoplakia, a leucoplakiform condition, cutaneous or mucosal (buccal) lichen, psoriasis, arthropathia psoriatica, cutaneous atopy, eczema, respiratory atopy, gingival hypertrophy, arthritis, a dermal or epidermal proliferation, common warts, flat warts, epidermodysplasia verruciformis, oral or florid papillomatoses, basal cell or prickle cell epithelioma, vesicular dermatoses, a collagen disease, corneopathies, skin aging, actinic keratosis or pigmentation, epidermal and/or dermal atrophy, cutaneous atrophy, cicatrization, stretch marks, a disorder of sebaceous function, hyperseborrhoea, cancerous or precancerous conditions, viral skin infection, alopecia, arteriosclerosis, skin benign summer leucitis, light-induced herpes labialis, solar erythema or light-induced immunosuppressant conditions.

* * * * *